United States Patent [19]
Arretz et al.

[11] Patent Number: 4,565,893
[45] Date of Patent: Jan. 21, 1986

[54] PROCESS OF SYNTHESIS OF MERCAPTANS FROM OLEFINS AND HYDROGEN SULPHIDE BY HETEROGENEOUS CATALYSIS

[75] Inventors: Emmanuel Arretz, Pau; Alfred Mirassou, Lescar; Claude Landoussy; Patrick Augé, both of Pau, all of France

[73] Assignee: Societe Nationale Elf Aquitaine (Production), France

[21] Appl. No.: 520,201

[22] Filed: Aug. 4, 1983

[30] Foreign Application Priority Data

Aug. 5, 1982 [FR] France ................................ 82 13689

[51] Int. Cl.$^4$ ........................................... C07D 221/18
[52] U.S. Cl. ...................................... 568/72; 568/73
[58] Field of Search ................................... 568/72, 73

[56] References Cited

U.S. PATENT DOCUMENTS 4,102,931  7/1978  Buchholz .............................. 568/73
4,347,384  8/1982  Fields .................................... 568/72

FOREIGN PATENT DOCUMENTS 160222  5/1983  Netherlands ......................... 568/72

OTHER PUBLICATIONS

Macho, Chem. Abst. vol. 95; 97053s, Equit. Czecho., 185469.

Primary Examiner—Donald G. Daus
Assistant Examiner—Cecilia Shen
Attorney, Agent, or Firm—Ostrolenk, Faber, Gerb & Soffen

[57] ABSTRACT

Process for the synthesis of a mercaptan from an olefin, by the action of hydrogen sulphide thereon, in the presence of a catalyst comprising a cation exchange resin, characterized in that this resin is dry and that the reaction is effected at a temperature ranging between 45° and 75° C.

15 Claims, No Drawings

PROCESS OF SYNTHESIS OF MERCAPTANS FROM OLEFINS AND HYDROGEN SULPHIDE BY HETEROGENEOUS CATALYSIS

The invention concerns a process for the synthesis of a mercaptan from an olefin, by the action of hydrogen sulphide thereon, in the presence of an insoluble catalyst. The invention relates particularly to a process in which the catalyst is constituted by a cation exchanger, namely a cation exchange resin. This novel process is particularly suitable for the production of tertiary mercaptans, especially tertiododecylmercaptan from tetrapropylene or tri-isobutylene.

The industrial utility of various mercaptans has meant that production processes have been closely studied for about 30 years. Also, technical literature includes numerous documents on this question. The processes first employed were based on catalysis in a homogeneous medium by acid compounds, particularly Lewis acids and most particularly aluminium chloride and boron fluoride. For obvious reasons, ways were sought to replace these soluble catalysts with insoluble catalytic mineral materials, particularly based on silica and alumina. The latter require elevated temperatures and give yields leaving much to be desired. An advance was made with the utilization of silico-aluminates in a special form, namely zeolites. Such a process is described in French Patent Publication No. 2391197. However, it is necessary even then to work at relatively elevated temperatures, of the order of 90° C. at least, to have viable industrial productivities. The activity of the catalyst drops appreciably, after about 100 hours of use, in the presence of the water contained in the reactants, which necessitates frequent regeneration of the catalyst and rigorous drying of the reactants.

It appears that research workers have previously tried to utilize organic cation exchangers; thus, Czechoslovak Pat. No. 185469 recommends the use of exchange resins based on styrene-divinylbenzene or phenol-formaldehyde copolymers. However, it appears that, in the operative conditions employed, such resins mainly catalyse reaction of the mercaptan with the olefin to give a thioether and much less that of the $H_2S$ with the olefin giving the mercaptan. This is doubtless the reason why the yields of thiols according to the Czechoslovak patent (Ex. 3 and 4) are very low whilst, in contrast, those of the thioether attain 80%.

This production also requires, according to the writers, a certain appreciable moisture content and a temperature of at least 80° C. In fact, whilst the document in question refers both to the synthesis of thioethers and of thiols, the latter appears to be impossible industrially in the presence of ion exchange resins. On the other hand, despite the assertion in most prior patents that the preparation of mercaptans can take place over a wide range of temperatures, notably between 20° and 200° C. or 50° to 150° C., it has not been possible to obtain industrial results by known processes at temperatures below 90° C.

Contrary to the bulk of the prior art, the process according to the invention provides the unexpected improvement of allowing the production of mercaptans, with excellent results, at materially lower temperatures, particularly below 80° C., with, as a catalyst, a cation exchange resin. Because of operation at very moderate temperatures, the catalyst remains active for very long periods and does not lead to reduction in the yield after about 100 hours, as is the case with other catalysts. It is equally surprising, in view of the statements made in the Czechoslovak patent mentioned above, that the process according to the invention, utilizing a cation exchange resin, allows the production of very pure thiols, with good yields and with a selectivity in practice of 100%.

The invention results from the discovery, contrary to the prior art, that cation exchange resins can well catalyze the addition of $H_2S$ to olefins to give mercaptans with excellent yields and purity, provided the resin is sufficiently dry and the temperature is controlled between the rigorous limits of 45° to 75° C. or, preferably, between 50° and 70° C.

Thus, the new process according to the invention consists in contacting hydrogen sulphide with one or more olefins in the presence of a cation exchange resin free from moisture as far as possible, at a temperature of 45° to 75° C., preferably under a relative pressure of 1 to 50 bars.

The operation can be conducted according to an operative mode known per se; it can be carried out discontinuously by injection of the olefin and $H_2S$ into a reactor containing a charge of ion exchange resin, heated to the desired temperature, for the necessary time, after which the liquid formed is separated in known manner. It is also possible to operate continuously in a tubular reactor of sufficient length, charged with the exchange resin and fed at one of its ends with a stream of the olefin and $H_2S$, the product of the reaction being recovered at the other end of the tube in order to be purified.

As regards the catalyst, in the process according to the invention, various polymers and copolymers having an acid function are suitable, which are known in the art as cation exchangers. In particular, use can be made of sulphonated polystyrene-based resins, cross-linked in particular with divinylbenzene, acrylic or phenylacrylic resins having free carboxyl groups, resins of the phenolformaldehyde type derived from phenolsulphonic acids, lignosulphonic exchangers etc. Resins of this kind are available commercially under various names, in particular Allassion, Cecacit, Wofatites and Levatites, Imac, Ionac, Amberlites, Liquorex, Zeorex, Zeocarb, Dowex, etc. Copolymers of sulphonated styrene with divinylbenzene are particularly suitable, for example those available commercially under the names Amberlyst, Lewatit or Dowex; on the other hand, copolymers of tetrafluoroethylene with perfluorosulphonic acid can be advantageously employed, in particular perfluoro-3,6-dioxa-4-methyl-7-octene-sulphonic acid known under the trade name Nafion.

Because one of the essential conditions of the invention is maximum dryness of the resin employed as the catalyst, it is necessary to ensure that this resin does not contain more than 0.5% of water determinable by drying at 80° for 6 hours and, preferably, 0.01% to 0.2%.

Whilst it is useful for chemical reasons to carry out the synthesis under elevated pressure, for example at 50 bars, the invention allows operation at moderate pressures, particularly 10 to 16 bars, namely in technologically simple conditions, whilst still obtaining excellent results. However, it is possible to operate at any relative pressure between 1 and 50 bars, the range from 10 to 16 bars being the most favourable industrially.

As in the known processes, it is suitable to use a sufficient excess of hydrogen sulphide; practical $H_2S$/olefin molar ratios range from 1.2 to 10 and preferably from 2 to 5.

The non-limitative examples which follow illustrate the invention.

EXAMPLE 1

In a tubular reactor having a length of 135 mm and an interior diameter of 20 mm, namely a volume of 420 ml, 200 ml of dry sulphonated resin of the styrene-divinylbenzene copolymer (Amberlyst 15) is placed. Under a pressure of 10 bars, liquid tetrapropylene is continuously introduced into this reactor at the rate of 121 g/h; at the same time, 73 g/h of gaseous $H_2S$ is injected. The reaction medium is maintained at the temperature of $60°\pm2°$ C. The reactants are intimately mixed before passing into the reactor. The liquid flowing continuously in the reactor is recovered and the remaining hydrogen sulphide is removed.

In the liquid obtained, 8% of non-converted tetrapropylene is found, the remainder being tertiododecylmercaptan; this is thus obtained at a conversion rate of the olefin of 92%, with a selectivity of 100%.

A similar operation is carried out, with the sole difference that the catalyst contains 1.6% of moisture, the conversion of the tetrapropylene then being no more than 80%.

EXAMPLE 2

A similar preparation to that of Example 1 is carried out in the same reactor, but with feed rates for the reactants which are halved; thus 60 g/h of tetrapropylene and 36.7 g/h of hydrogen sulphide are introduced, at 10 bars. Conversion of the tetrapropylene is then 96% and the selectivity of the tertiododecyl-mercaptan obtained is 100%. As production of the mercaptan still represents 69.25 g/h per liter of catalyst space, the operative conditions are completely acceptable industrially and give a very good yield with a perfect purity of the product. As no impurity forms, the unconverted tetrapropylene is readily recyclable.

In the same operative conditions, but with moist Amberlyst 15 resin, conversion of the tetrapropylene falls to 85%.

EXAMPLE 3

In the same reactor as before, use is made of 100 g of dry perfluorosulphonic acid resin. 60 g/h of tetrapropylene and 36.7 g/h of hydrogen sulphide are introduced, at 10 bars. At the outlet from the reactor, a conversion of the tetrapropylene of 90% is obtained, with a selectivity of tertiododecylmercaptan practically of 100%.

EXAMPLE 4

Operating with 120 g of Amberlyst 15 resin, 40 g/h of isobutene and 73 g/h of hydrogen sulphide are introduced into the reactor at a pressure of 10 bars. The reaction temperature is 70° C. 63 g/h of tertiobutylmercaptan is obtained, namely a conversion of 98% to this product.

EXAMPLE 5

Operation took place as in Example 1, with dry Amberlyst 15 resin and input rates of 121 g/h of tetrapropylene and 73 g/h of hydrogen sulphide at a temperature of 60° C. The experiment was continued for 700 hours without modification of the conversion of the tetrapropylene, which remained at 91%–92%.

We claim:

1. Process for the synthesis of a mercaptan from an olefin, by the action of hydrogen sulphide thereon, in the presence of a catalyst comprising a polymer or copolymer cation exchange resin selected from the group consisting of cross-linked sulfonated polystyrene, acrylic and phenylacrylic resin having free carboxyl groups, phenolsulfonic acid-formaldehyde resin, lignosulfonic resin and copolymer of tetrafluoroethylene and perfluorosulfonic acid, characterized in that the resin is dry containing not more than 0.5% water determinable by drying at 80° for six hours and that the reaction is carried out at a temperature ranging between 45° and 75° C.

2. Process according to claim 1, characterized in that the temperature is maintained between 50° and 70° C.

3. Process according to claim 1 or 2, in which the cation exchange resin is a copolymer of sulphonated styrene with divinylbenzene.

4. Process according to claim 1 or 2, characterized in that the cation exchange resin comprises a copolymer of tetrafluoroethylene with perfluorosulphonic acid.

5. Process according to claim 1, in which the reaction medium is maintained at a pressure of 1 to 50 bars.

6. Process according to claim 1, characterized in that the moisture content is from 0.01% to 0.2%.

7. Process according to of claim 1, in which the olefin is tetrapropylene.

8. Process according to claim 7 wherein the temperature is maintained between 50° and 70° C. and the pressure is 1 to 50 bars.

9. Process according to claim 8 in which the $H_2S$/olefin molar ratio is 1.2–10.

10. Process according to claim 9 in which the pressure is 10–16 bars, the $H_2$/S olefin ratio is 2–5, and the moisture content of the dry cation exchange resin is from 0.01% to 0.2%.

11. Process according to claim 10 in which the cation exchange resin is a copolymer of sulfonated styrene with divinylbenzene.

12. Process according to claim 10 in which the cation exchange resin is perfluorosulfonic acid tetrafluoroethylene copolymer resin.

13. Process according to claim 1 in which the reaction medium is maintained at a pressure of 1 to 50 bars.

14. Process according to claim 1 in which the $H_2S$/olefin molar ratio is 1.2–10.

15. Process according to claim 14 in which the ratio is 2–5.

* * * * *